(12) United States Patent
Edwards et al.

(10) Patent No.: US 8,544,645 B2
(45) Date of Patent: Oct. 1, 2013

(54) DEVICES, SYSTEMS AND METHODS FOR MEDICAMENT DELIVERY

(75) Inventors: Eric Shawn Edwards, Midlothian, VA (US); Evan Thomas Edwards, Fredericksburg, VA (US); Mark J. Licata, Doswell, VA (US); T. Spencer Williamson, Richmond, VA (US)

(73) Assignee: Intelliject, Inc., Richmond, VA (US)

( * ) Notice: Subject to any disclaimer, the term of this patent is extended or adjusted under 35 U.S.C. 154(b) by 0 days.

(21) Appl. No.: 13/464,234

(22) Filed: May 4, 2012

(65) Prior Publication Data

US 2012/0280815 A1 Nov. 8, 2012

Related U.S. Application Data

(63) Continuation of application No. 11/671,025, filed on Feb. 5, 2007, now Pat. No. 8,172,082, which is a continuation-in-part of application No. 11/621,236, filed on Jan. 9, 2007, now Pat. No. 7,731,686, which is a continuation-in-part of application No. 10/572,148, filed as application No. PCT/US2006/003415 on Feb. 1, 2006, now Pat. No. 7,749,194.

(60) Provisional application No. 60/648,822, filed on Feb. 1, 2005, provisional application No. 60/731,886, filed on Oct. 31, 2005, provisional application No. 60/787,046, filed on Mar. 29, 2006.

(51) Int. Cl.
*B65D 83/10* (2006.01)

(52) U.S. Cl.
USPC ............ 206/364; 206/363; 206/365; 604/189

(58) Field of Classification Search
USPC .................................. 604/189; 206/363–370
See application file for complete search history.

(56) References Cited

U.S. PATENT DOCUMENTS 2,960,087 A 11/1960 Uytenbogaart
3,055,362 A 9/1962 Uytenbogaart (Continued)

FOREIGN PATENT DOCUMENTS

EP 1043037 A2 10/2000
EP 1287840 A1 3/2003

(Continued)

OTHER PUBLICATIONS

"Solutions for Medical Devices," © 3M Brochure, © 3M 2006 80-6201-3490-0.

(Continued)

*Primary Examiner* — Emily Schmidt
(74) *Attorney, Agent, or Firm* — Cooley LLP

(57) ABSTRACT

An apparatus includes a container defining an internal region configured to contain multiple medicament delivery devices, such as, for example, pen injectors, auto-injectors, inhalers or the like. The container includes an electronic circuit system configured to output a first electronic output associated with a first medicament delivery device contained within the internal region when the first medicament delivery device is removed from the internal region of the container. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction.

17 Claims, 8 Drawing Sheets

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,149,394 A | 4/1979 | Sornes |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,466,217 A | 11/1995 | Myers et al. |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci et al. |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,284,765 B1 | 9/2001 | Caffrey |
| 6,312,412 B1 | 11/2001 | Saied et al. |
| 6,317,630 B1 | 11/2001 | Gross et al. |
| 6,321,654 B1 | 11/2001 | Robinson |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |

| | | |
|---|---|---|
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Sahar et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang et al. |
| 6,554,798 B1 | 4/2003 | Mann et al. |
| 6,558,320 B1 | 5/2003 | Causey, III et al. |
| 6,560,471 B1 | 5/2003 | Heller et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,659,980 B2 | 12/2003 | Moberg et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,093,595 B2 | 8/2006 | Nesbitt |
| 7,113,101 B2 | 9/2006 | Petersen et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,670,328 B2 | 3/2010 | Miller et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,172,082 B2 | 5/2012 | Edwards et al. |
| 8,231,573 B2 | 7/2012 | Edwards et al. |
| 2001/0005781 A1 | 6/2001 | Bergens et al. |
| 2002/0072784 A1 | 6/2002 | Sheppard, Jr. et al. |
| 2002/0074345 A1* | 6/2002 | Schneider et al. ............ 222/94 |
| 2002/0076679 A1 | 6/2002 | Aman |
| 2002/0090601 A1 | 7/2002 | Strupat et al. |
| 2002/0096543 A1 | 7/2002 | Juselius |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0106824 A1 | 6/2003 | Wilmot et al. |
| 2003/0132128 A1 | 7/2003 | Mazur |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0069667 A1* | 4/2004 | Tomellini et al. ............ 206/364 |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1* | 8/2005 | Veit et al. .................. 604/93.01 |
| 2005/0186221 A1 | 8/2005 | Reynolds et al. |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |

| | | | |
|---|---|---|---|
| 2006/0169611 A1 | 8/2006 | Prindle | |
| 2006/0189938 A1 | 8/2006 | Hommann et al. | |
| 2006/0200077 A1 | 9/2006 | Righi et al. | |
| 2006/0247579 A1 | 11/2006 | Friedman | |
| 2006/0265186 A1 | 11/2006 | Holland et al. | |
| 2007/0008113 A1 | 1/2007 | Spoonhower et al. | |
| 2007/0074722 A1 | 4/2007 | Giroux et al. | |
| 2007/0184847 A1 | 8/2007 | Hansen et al. | |
| 2007/0203247 A1 | 8/2007 | Phillips et al. | |
| 2007/0210147 A1 | 9/2007 | Morrone et al. | |
| 2007/0213598 A1 | 9/2007 | Howard et al. | |
| 2007/0233001 A1 | 10/2007 | Burroughs et al. | |
| 2007/0239116 A1 | 10/2007 | Follman et al. | |
| 2007/0260210 A1 | 11/2007 | Conroy | |
| 2008/0059133 A1 | 3/2008 | Edwards et al. | |
| 2008/0111685 A1* | 5/2008 | Olson et al. | 340/545.6 |
| 2008/0160492 A1 | 7/2008 | Campbell et al. | |
| 2008/0230057 A1* | 9/2008 | Sutherland | 128/202.13 |
| 2009/0024112 A1 | 1/2009 | Edwards et al. | |
| 2009/0176834 A1 | 7/2009 | Kottayil et al. | |
| 2009/0240200 A1 | 9/2009 | Heneveld et al. | |
| 2010/0211005 A1 | 8/2010 | Edwards et al. | |
| 2012/0008811 A1 | 1/2012 | Edwards et al. | |
| 2012/0226226 A1 | 9/2012 | Edwards et al. | |
| 2013/0023822 A1 | 1/2013 | Edwards et al. | |
| 2013/0023825 A1 | 1/2013 | Edwards et al. | |

FOREIGN PATENT DOCUMENTS

| | | |
|---|---|---|
| EP | 1462134 A1 | 9/2004 |
| EP | 1712178 A2 | 10/2006 |
| JP | 55-75335 | 6/1980 |
| JP | 2003-310758 | 11/2003 |
| JP | 2006-034845 | 2/2006 |
| WO | WO 91/04760 A1 | 4/1991 |
| WO | WO93/02720 | 2/1993 |
| WO | WO 95/26009 | 9/1995 |
| WO | WO 97/30742 | 8/1997 |
| WO | WO 99/07425 | 2/1999 |
| WO | WO 99/43283 | 9/1999 |
| WO | WO 01/24690 A2 | 4/2001 |
| WO | WO 01/26020 A1 | 4/2001 |
| WO | WO 01/41849 A2 | 6/2001 |
| WO | WO 01/88828 | 11/2001 |
| WO | WO 01/93926 A2 | 12/2001 |
| WO | WO 02/24257 A1 | 3/2002 |
| WO | WO 02/051471 A1 | 7/2002 |
| WO | WO 03/057283 A1 | 7/2003 |
| WO | WO 03/095001 A1 | 11/2003 |
| WO | WO 03/097133 A1 | 11/2003 |
| WO | WO 2004/041330 A2 | 5/2004 |
| WO | WO 2005/050526 A2 | 6/2005 |
| WO | WO 2006/045525 A1 | 5/2006 |
| WO | WO 2006/109778 A1 | 10/2006 |
| WO | WO2006/125692 | 11/2006 |

OTHER PUBLICATIONS

Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947 >.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >.

"Flex Circuits/flexible circuits design guide," [online] [retrieved on Aug. 28, 2006] Retrieved from the Internet <URL: http://flexiblecircuit.co.uk/Flex Circuits Design Guide.htm >.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp >.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.

Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.

Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true.

Heartsine Technology, samaritan™ Pad Accessories [online] [retrieved on Jun. 1, 2007] Retrieved from the Internet <URL: http://www.heartsine.com/aboutsam-accessories.htm>.

CliniSense Corporation, "Drug delivery devices a potentially harsh environment for drugs," Stability [online] [retrieved on Jun. 1, 2007] Retrieved from the Internet <URL: http://www.clinisense.com/devices.htm>.

CliniSense Corporation, "LifeTrack Technology a new method to detect improper storage." Stability [online] [retrieved on Jun. 1, 2007] Retrieved from the Internet <URL: http://www.clinisense.com/tech.htm>.

AED Professionals™ Brochure [online] [retrieved on Jun. 1, 2007] Retrieved from the Internet <URL: http://www.aedprofessionals.com/>.

Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >.

Search Report and Written Opinion for International Patent Application No. PCT/US06/03415 mailed Jul. 13, 2006, 10 pages.

Search Report and Written Opinion for International Patent Application No. PCT/US07/007626 mailed Sep. 29, 2008.

Combined Search and Examination Report for GB 0818178.6, mailed Dec. 1, 2008.

Office Action for U.S. Appl. No. 11/621,236, mailed Feb. 3, 2009.

Examination Report for British Patent Application No. GB 0818178.6, mailed Mar. 23, 2009.

Examination Report for British Patent Application No. GB 0905194.7, mailed May 8, 2009.

Final Office Action for U.S. Appl. No. 11/621,236, mailed Jul. 1, 2009.

Examination Report for British Patent Application No. GB 0818178.6, mailed Jul. 9, 2009.

Search Report and Written Opinion for International Patent Application No. PCT/US09/63983, mailed Feb. 25, 2010.

Search Report for European Patent Application No. 09150135.3, mailed Mar. 15, 2010.

Final Office Action for U.S. Appl. No. 11/679,331, mailed Feb. 15, 2011.

Office Action for Japanese Patent Application No. JP2009-502964, mailed May 23, 2011.

Final Office Action for U.S. Appl. No. 11/671,025, mailed Sep. 8, 2011.

English Translation of Office Action for Japanese Patent Application No. 2011-509613, mailed May 15, 2013.

Non-Final Office Action for U.S. Appl. No. 13/036,720, mailed May 17, 2013.

Non-Final Office Action for U.S. Appl. No. 13/234,649, mailed May 28, 2013.

English Translation of Office Action for Indian Patent Application No. 5414/DELNP/2007, mailed May 21, 2013.

* cited by examiner

DEVICES, SYSTEMS AND METHODS FOR MEDICAMENT DELIVERY

CROSS-REFERENCE TO RELATED APPLICATIONS

This application is a continuation of U.S. patent application Ser. No. 11/671,025, entitled "Devices, Systems and Methods for Medicament Delivery," filed Feb. 5, 2007, which is a continuation-in-part of U.S. patent application Ser. No. 11/621,236, now U.S. Pat. No. 7,731,686, entitled "Devices, Systems and Methods for Medicament Delivery," filed Jan. 9, 2007, which claims priority to U.S. Provisional Application Ser. No. 60/787,046, entitled "Devices, Systems and Methods for Medicament Delivery," filed Mar. 29, 2006, which is incorporated herein by reference in its entirety. U.S. patent application Ser. No. 11/621,236 is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety.

BACKGROUND

The invention relates generally to a medical device, and more particularly to a container for containing medicament delivery devices.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

For a variety of reasons, however, some individuals who are susceptible to allergic reactions may not carry such a medicament delivery device. For example, some individuals may not be aware of their susceptibility to allergic reactions. Other individuals may be are aware of their susceptibility but may, at times, forget to carry a medicament delivery device and/or leave it in a location where it is impractical to use in an emergency. In some situations, the consequences of an individual leaving home without having a medicament delivery device can be compounded when, for example, the individual is going to an environment that poses a greater likelihood of exposure to the substances that can trigger an allergic reaction. For example, an individual who is allergic to peanuts may be at a much greater risk when eating at a restaurant than when eating at home.

Moreover, some known medicament delivery devices require several steps to deliver the medicament into the patient. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. In certain instances, for example, users who have become confused in the operation of some known auto-injectors have inadvertently injected the medicament into their thumb by improperly positioning the auto-injector.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic and/or the physiological effects of the condition requiring treatment.

Some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, inhalers or the like, can be compact, such printed instructions may be too small to read and comprehend during an emergency situation.

Thus, a need exists for a container for medicament delivery devices that can be located in environments in which some individuals may have a higher than normal risk of having an allergic reaction. Additionally, such containers should provide instructions for using the medicament delivery devices contained therein that can be easily understood by an untrained user in any type of situation.

SUMMARY

Apparatuses for containing medicament delivery devices are described herein. In one embodiment, an apparatus includes a container defining an internal region configured to contain multiple medicament delivery devices, such as, for example, pen injectors, auto-injectors, inhalers or the like. The container includes an electronic circuit system configured to output a first electronic output associated with a first medicament delivery device contained within the internal region when the first medicament delivery device is removed from the internal region of the container. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction of the first medicament delivery device and/or the second medicament delivery device.

DETAILED DESCRIPTION

Figure 1:
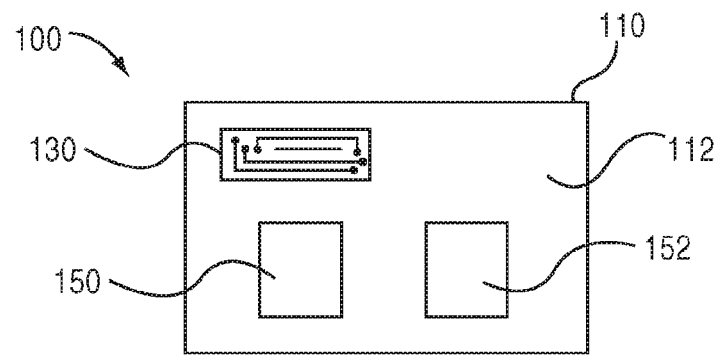
FIGS. 1-3 are schematic illustrations of a medical device according to an embodiment of the invention in a first configuration, a second configuration and a third configuration, respectively.

In some embodiments, an apparatus includes a container defining an internal region configured to contain multiple medicament delivery devices, such as, for example, pen injectors, auto-injectors, inhalers or the like. The container includes an electronic circuit system configured to output a first electronic output associated with a first medicament delivery device contained within the internal region when the first medicament delivery device is removed from the internal region of the container. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction of the first medicament delivery device and/or the second medicament delivery device.

In some embodiments, an apparatus includes a container defining an internal region configured to contain multiple medicament delivery devices. The container includes an electronic circuit system configured to output a first electronic output associated with a first medicament delivery device contained within the internal region when the first medicament delivery device is removed from the internal region of the container. The first medicament delivery device includes a label configured to output a signal associated with at least one of a contents of the first medicament delivery device, an expiration date of the first medicament delivery device, a dosage of the first medicament delivery device or a use instruction associated with the first medicament delivery device. In this manner, the first electronic output can be associated with the signal received by the electronic circuit system. The electronic circuit system is further configured to output a second electronic output associated with a second medicament delivery device contained within the internal region when the second medicament delivery device is removed from the internal region of the container. The second electronic output is different than the first electronic output. At least one of the first electronic output or the second electronic output is associated with a use instruction of the first medicament delivery device and/or the second medicament delivery device.

In some embodiments, a kit includes a medicament delivery device and a container. The container defines an internal region configured to contain the medicament delivery device. The container includes a movable portion, an electronic circuit system, a first switch and a second switch. The movable portion has a first position, in which the movable portion covers the internal region of the container, and a second position, in which the internal region of the container is exposed to an area outside the container. The first switch is configured to move between a first state and a second state when the movable portion moves between its first position and its second position. The first switch is operatively coupled to the electronic circuit system such that the electronic circuit system is configured to output a first electronic output when the first switch is moved from its first state to its second state. The first electronic output can be, for example, a visual output, an audible output or a haptic output. The second switch is configured to move between a first state and a second state when the medicament delivery device is removed from the internal region of the container. The second switch is operatively coupled to the electronic circuit system such that the electronic circuit system is configured to output a second electronic output when the second switch is moved from its first state to its second state. The second electronic output, which includes an instruction for using the medicament delivery device, can be, for example, a visual output (e.g. a video showing the proper use of the medicament delivery device), an audible output (e.g., a voice recording providing instructions for use) or a haptic output (e.g., a vibration indicating the location of a particular item).

In some embodiments, an apparatus includes a container, a retainer and an electronic circuit system. The container defines an internal region configured to contain at least a portion of a medicament delivery device, such as, for example a pen injector. The retainer is configured to be movably coupled to the container and to retain the portion of the medicament delivery device within the internal region defined by the container. The electronic circuit system is configured to output a first electronic output when the retainer is moved relative to the container and a second electronic output when the medicament delivery device is removed from the internal region. At least one of the first electronic output or the second electronic output is associated with an instruction for using the medicament delivery device.

In some embodiments, an apparatus includes a container, a retainer, an electronic circuit system and a label. The container defines an internal region configured to contain at least a portion of a medicament delivery device, such as, for example a pen injector. The retainer is configured to be movably coupled to the container and to retain the portion of the medicament delivery device within the internal region defined by the container. The label is configured to be coupled to the medicament delivery device and contain information associated with the medicament delivery device in a machine-readable format. The electronic circuit system is configured to output a first electronic output when the retainer is moved relative to the container and a second electronic output when the medicament delivery device is removed from the internal region. The electronic circuit system is further configured to receive the information contained on the label include at least a portion of the information in the first electronic output and/or the second electronic output. At least one of the first electronic output or the second electronic output is associated with an instruction for using the medicament delivery device.

Figure 2:
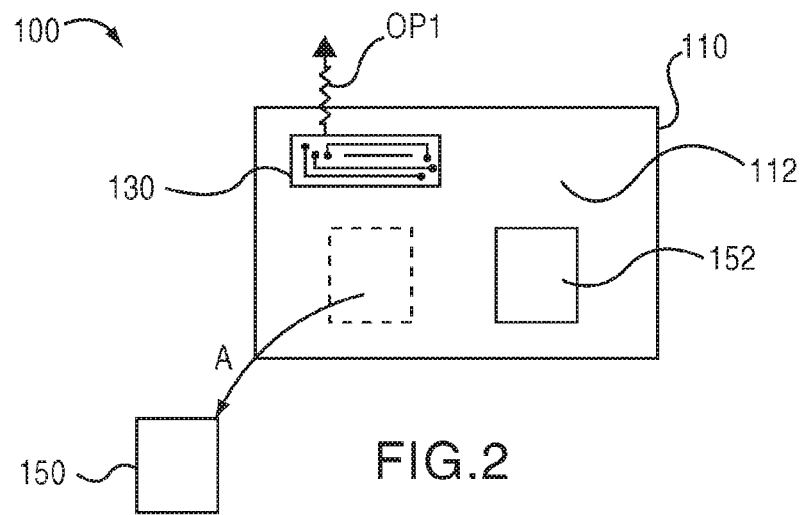
Figure 3:
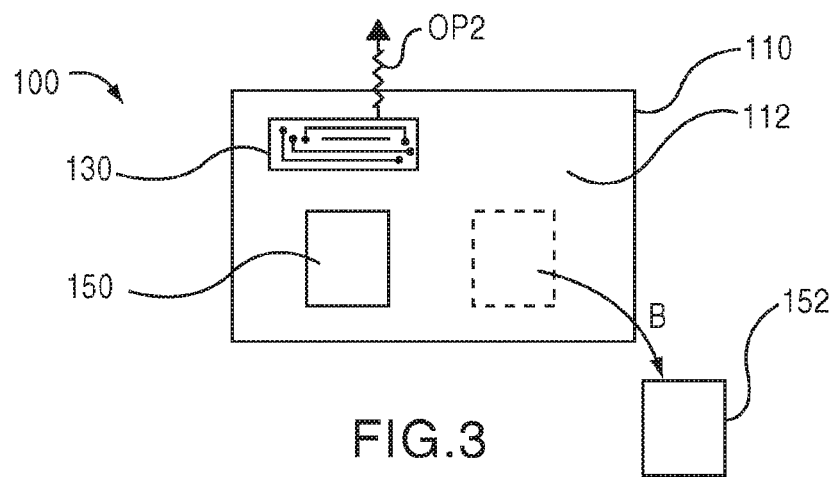

FIGS. 1-3 are schematic illustrations of a medical device 100 according to an embodiment of the invention in a first configuration, a second configuration and a third configuration, respectively. The medical device 100 includes a container 110 including an electronic circuit system 130 and defining an internal region 112. The internal region 112 is configured to contain one or more medicament delivery devices. Disposed within the internal region 112 are at least a first medicament delivery device 150 and a second medicament delivery device 152. The first medicament delivery device 150 and/or the second medicament delivery device 152 can be any suitable medicament delivery device, such as, for example, an auto-injector, a pen injector, an inhaler or the like.

As shown in FIG. 2, the electronic circuit system 130 is configured to output a first electronic output OP1 when the first medicament delivery device 150 is removed from the internal region 112 of the container 110, as indicated by the arrow A. As discussed in more detail herein, the first electronic output OP1 can be associated with an identification of the first medicament delivery device 150, an identification of a physical condition and/or an instruction for using the first medicament delivery device 150. Moreover, the first electronic output OP1 can include a visual output, an audible output and/or a haptic output. For example, in some embodiments, the first electronic output OP1 can be associated with an audible message instructing a user in the use of the first medicament delivery device 150. Such an audible message can state, for example, "You have removed an auto-injector containing Epinephrine. To actuate the auto-injector, first remove the red safety tab located at the end of the auto-injector." In other embodiments, for example, the first electronic output OP1 can be associated with a visual text message instructing to perform a series of tests on and/or observe the symptoms exhibited by a patient to determine whether the patient is suffering from a certain physical condition (e.g., anaphylactic shock).

Similarly, as shown in FIG. 3, the electronic circuit system 130 is configured to output a second electronic output OP2 when the second medicament delivery device 152 is removed from the internal region 112 of the container 110, as indicated by the arrow B. The second electronic output OP2, which is different than the first electronic output OP1, can include a visual output, an audible output and/or a haptic output. Moreover, as with the first electronic output OP1, the second electronic output OP2 can be associated with at least one of an identification of the second medicament delivery device 152, an identification of a physical condition and/or an instruction for using the second medicament delivery device 152. In this manner, the electronic circuit system 130 can provide the user with information about the particular medicament delivery device that has been removed from the container 110.

Although the second electronic output OP2 is described as being different than the first electronic output OP1, in some embodiments, the second electronic output OP2 can be the same as the first electronic output OP1. In some embodiments, for example, the second electronic output OP2 can include the same information as previously output via the first electronic output OP1 along with additional information. In this manner, the second electronic output OP2 can confirm the instructions and/or information provided by the first electronic output OP1.

The container 110 can be any container suitable for containing a plurality of medicament delivery devices. For example, in some embodiments, the container 110 can be a box-like structure that includes a lid or cover that can be repeatedly opened and closed to selectively expose the internal region 112 of the container 110 to an area outside the container 110. In other embodiments, the container 110 can include a frangible portion that can be irreversibly moved to expose the internal region 112 of the container 110 to allow access to the first medicament delivery device 150 and/or the second medicament delivery device 152.

The container 110 can be either portable or permanently installed at a particular location. For example, in some embodiments, the container 110 can be configured to be moved by the user. For example, in such embodiments, a user may carry the container 110 to events, such as picnics, field trips, children's camps or the like, where the likelihood of use increases. In other embodiments, the container 110 can be removably coupled to a mounting area within a building, such as a restaurant, airport and/or shopping mall. In this manner, when a user recognizes an emergency situation, the user can locate the container 110 and move it to the area in which the emergency situation is occurring. In yet other embodiments, the container 110 can be permanently coupled to a wall of a building.

The container 110 can be constructed from any suitable material, such as, for example, plastic, metal alloys, insulative foam, fabric or any combination thereof. In some embodiments, for example, the container 110 can include a hard, plastic outer casing and an insulative, shock-absorbing inner liner. In some embodiments, the container 110 can be constructed from a waterproof material and/or can be configured to float. In some embodiments, the container 110 can be constructed from a material configured to prevent light from reaching the interior region 112 of the container. In this manner, the container can prevent the medicaments contained therein from being exposed to light that can impact the chemical structure and/or stability of the medicament.

Although the container 110 is shown and described above as containing a first medicament delivery device 150 and a second medicament delivery device 152 having similar sizes and/or shapes, in some embodiments, a container can be configured to include medicament delivery devices of different sizes and/or shapes. For example, in some embodiments, a container can be configured to include a medical injector having a long, narrow shape and an inhaler having a wider shape.

Figure 4:
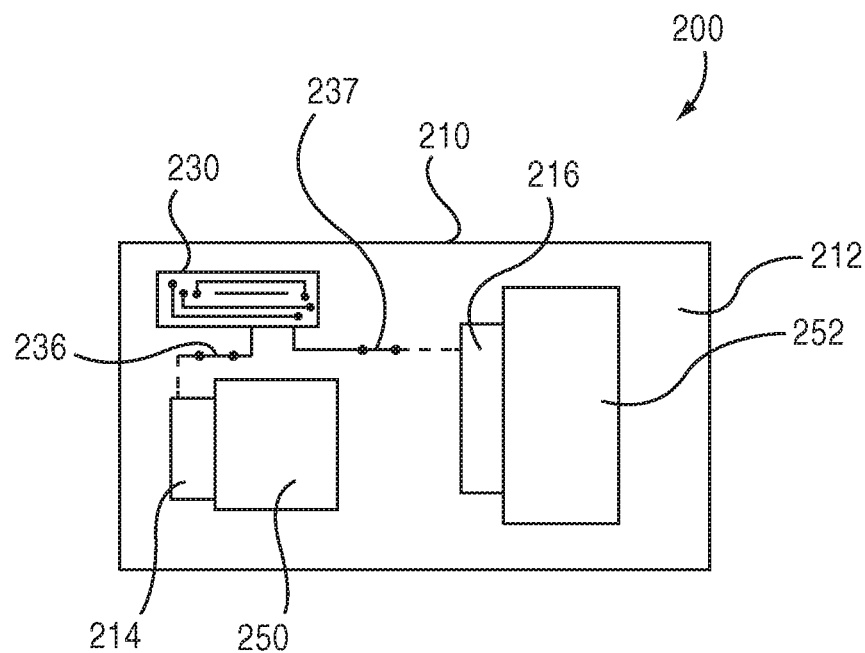
FIGS. 4-6 are schematic illustrations of a medical device according to an embodiment of the invention in a first configuration, a second configuration and a third configuration, respectively.
Figure 5:
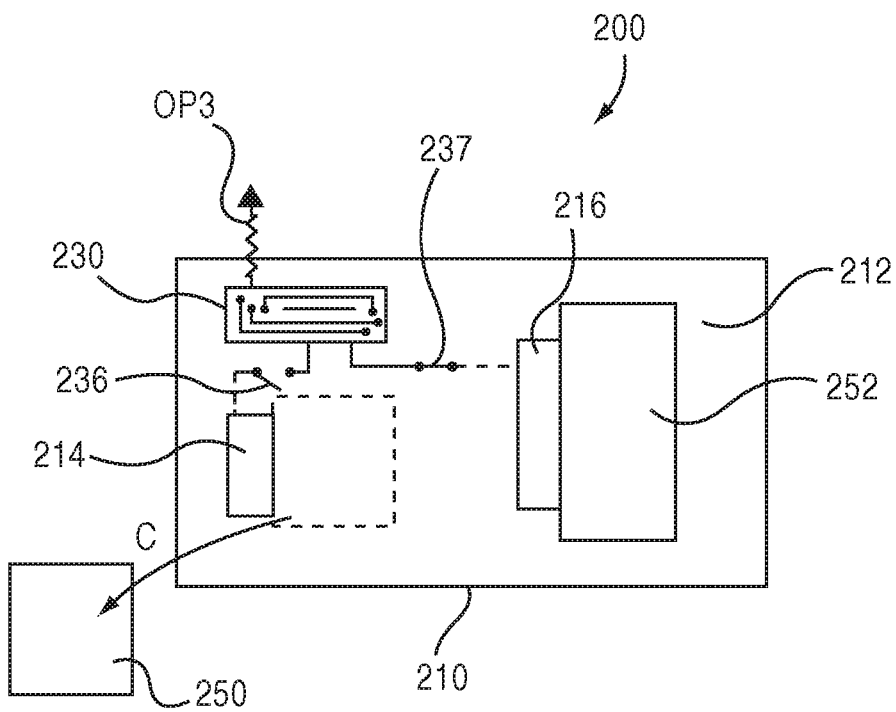
Figure 6:
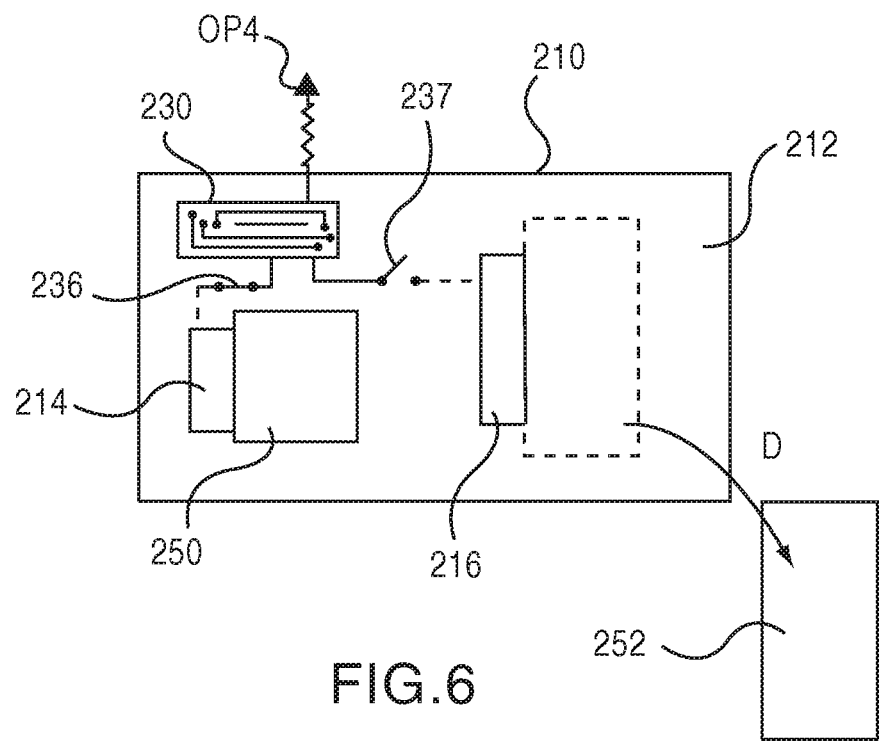

FIGS. 4-6 are schematic illustrations of a medical device 200 according to one such embodiment of the invention in a first configuration, a second configuration and a third configuration, respectively. The medical device 200 includes a container 210 including an electronic circuit system 230 and defining an internal region 212. The internal region 212 includes a first retainer 214 and a second retainer 216. The first retainer 214 retains a first medicament delivery device 250 within the internal region 212 of the container. Similarly, the second retainer 216 retains a second medicament delivery device 252 within the internal region 212 of the container.

The electronic circuit system 230 includes a first switch 236 associated with the first retainer 214 and a second switch 237 associated with the second retainer 216. The first switch 236 is configured move between a first state (e.g., closed) and a second state (e.g., opened) when the first medicament delivery device 250 is removed from the first retainer 214. Similarly, the second switch 237 is configured move between a first state and a second state when the second medicament delivery device 252 is removed from the second retainer 216.

In this manner, the electronic circuit system 230 can output electronic outputs based on the state of the first switch 236 and/or the second switch 237.

More particularly, as shown in FIG. 5, the electronic circuit system 230 is configured to output a first electronic output OP3, of the type described above, when the first medicament delivery device 250 is removed from the first retainer 214, as indicated by the arrow C. Similarly, as shown in FIG. 6, the electronic circuit system 230 is configured to output a second electronic output OP4, of the type described above, when the second medicament delivery device 252 is removed from the second retainer 216, as indicated by the arrow D. Said another way, the electronic circuit system 230 is configured to output the first electronic output OP3 in response to the first switch 236 moving between its first state and its second state. Similarly, the electronic circuit system 230 is configured to output the second electronic output OP4 in response to the second switch 237 moving between its first state and its second state.

The first retainer 214 can be any structure that cooperates with the first medicament delivery device 250 to retain the first medicament delivery device 250 within the internal region 212 of the container 210. Similarly, the second retainer 216 can be any structure that cooperates with the second medicament delivery device 252 to retain the second medicament delivery device 252 within the internal region 212 of the container 210. In some embodiments, for example, the first retainer 214 can be a recessed portion (not shown in FIGS. 4-6) of the internal region 212 having a shape to receive at least a portion of the first medicament delivery device 250. Such a recess can include, for example, an edge, a contour or a ridge that forms an interference fit with a portion of the first medicament delivery device 250 when the first medicament delivery device 250 is received within the first retainer 214. In other embodiments, for example, the first retainer 214 and/or the second retainer 216 can be a clip configured to engage a portion of the first medicament delivery device 250 and/or the second medicament delivery device 252, respectively, to retain the first medicament delivery device 250 and/or the second medicament delivery device 252 in the internal region 212. In yet other embodiments, the first retainer 214 and/or the second retainer 216 can be an elastic member, such as an elastic band configured to engage a portion of the first medicament delivery device 250 and/or the second medicament delivery device 252. In yet other embodiments, the first retainer 214 and/or the second retainer 216 can include a frangible member, such as a removable plastic covering configured to retain the first medicament delivery device 250 and/or the second medicament delivery device 252 in the internal region 212.

In some embodiments, the first retainer 214 can be uniquely associated with the first medicament delivery device 250 and/or the second retainer 214 can be uniquely associated with the second medicament delivery device 252. In this manner, the first medicament delivery device 250 can only be associated with the first switch 236 and the second medicament delivery device 252 can only be associated with the second switch 237. Said another way, such an arrangement prevents second medicament delivery 252 from inadvertently being retained by the first retainer 214, which could result in the electronic circuit system 230 outputting the first electronic output OP3 when the second medicament delivery device 252 is removed from the container 210 or vice-versa. Moreover, by using the first retainer 214 and the second retainer 216, the internal region 212 can be adapted to contain a variety of different medicament delivery devices having different sizes, shapes and/or characteristics. For example, in those embodiments in which the first retainer 214 is a recessed portion of the internal region 212, the shape of the recess can be uniquely associated with a shape of the first medicament delivery device 250, thereby preventing the second medicament delivery device 252 from being received within the first retainer 214. Similarly, in some embodiments, the second retainer 216 can be a recessed portion of the internal region 212, of the type described above, having a shape to receive at least a portion of the second medicament delivery device 252.

Although the retainers are described above as cooperating with the medicament delivery devices to retain the medicament delivery devices within the internal region 212 of the container 210, in some embodiments, the first retainer 214 and/or the second retainer 216 can perform additional functions. For example, in some embodiments, the first retainer 214 can electronically couple an electronic circuit system (not shown in FIGS. 4-6) disposed on the first medicament delivery device 250 to the electronic circuit system 230. The electronic circuit system included in the first medicament delivery device 250 can be of the type shown and described in U.S. patent application Ser. No. 11/621,236, entitled "Devices, Systems and Methods for Medicament Delivery," filed Jan. 9, 2007, which is incorporated herein by reference in its entirety. Similarly, the second retainer 216 can electronically couple an electronic circuit system (not shown in FIGS. 4-6) disposed on the second medicament delivery device 252 to the electronic circuit system 230. In this manner, the first retainer 214 and/or the second retainer 216 can be used as a battery charging port, a data exchange port or the like.

Figure 7:
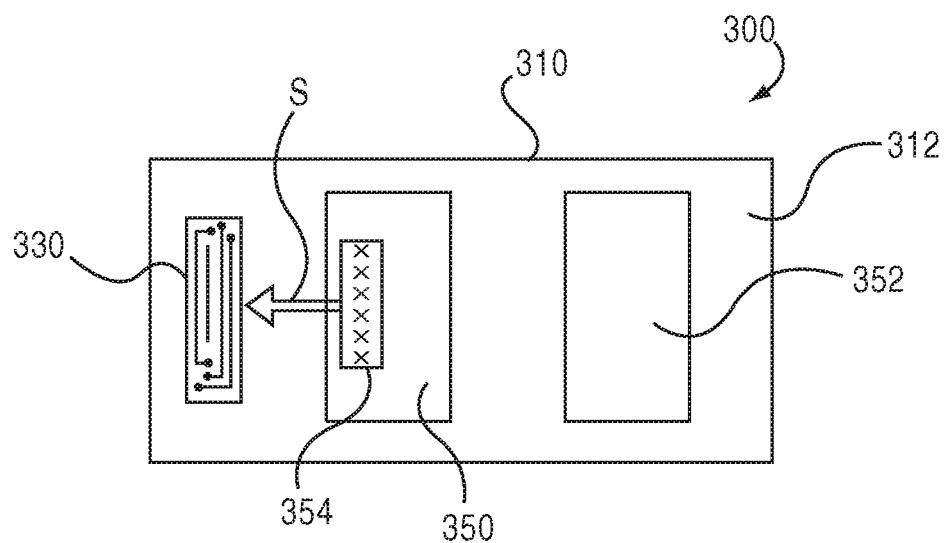
FIG. 7 is a schematic illustration of a medical device according to an embodiment of the invention.

FIG. 7 is a schematic illustration of a medical device 300 according to an embodiment of the invention. Because the medical device 300 is similar in many respects to the medical devices shown and described above, the medical device 300 is shown in only one configuration. The medical device 300 includes a container 310 including an electronic circuit system 330 and defining an internal region 312. The internal region 312 includes a first medicament delivery device 350 and a second medicament delivery device 352 of the types described above.

The electronic circuit system 330 is configured to output a first electronic output (not shown in FIG. 7), of the type described above, when the first medicament delivery device 350 is removed from the internal region 312 of the container 310. Similarly the electronic circuit system 330 is configured to output a second electronic output (not shown in FIG. 7), of the type described above, when the second medicament delivery device 352 is removed from the internal region 312 of the container 310.

Moreover, as shown in FIG. 7, the first medicament delivery device 350 includes a label 354, such as, for example, a radio frequency identification ("RFID") tag, configured to output a signal S that can be received by the electronic circuit system 330. In some embodiments, the signal S can indicate the position of the first medicament delivery device 350 (e.g., whether the first medicament delivery device 350 is outside the internal region 312). In other embodiments, the signal S can include information characterizing the first medicament delivery device 350. For example, in some embodiments, the signal S can be associated with the contents of the first medicament delivery device 350 (e.g., the amount and type of medicament contained therein), an expiration date of the first medicament delivery device 350, a dosage of the first medicament delivery device 350 and/or a use instruction associated with the first medicament delivery device 350. In this manner, the electronic circuit system 330 can receive the signal S and produce the first electronic output (not shown in FIG. 7) to include information contained within the signal S.

Said another way, this arrangement allows the electronic circuit system 330 to produce an electronic output that is unique to the medicament delivery devices contained within the container 310.

In some embodiments, for example, the first electronic output can be associated with an audible message including information contained from the signal S, such as for example, the expiration date of the medicament contained within the first medicament delivery device 350. Such an audible message can state, for example, "You have removed an auto-injector containing DOSE mg of Epinephrine. The expiration date of this device is EXPIRATION DATE. If the current date is later than EXPIRATION DATE please select another auto-injector from within the container." In other embodiments, for example, the first electronic output can be a message providing the user with use instructions or other information contained within the signal S that is uniquely associated with the first medicament delivery device 350. For example, such a message can prompt a user to call a phone number unique to the manufacturer of the first medicament delivery device 350 for assistance before, during or after the use of the first medicament delivery device 350. In yet other embodiments, as described in more detail herein, the electronic circuit system 330 can automatically call such a phone number when the first medicament delivery device 350 is removed from the internal region 312 of the container 310.

The label 354 can be any device suitable for outputting the signal S that includes information associated with the first medicament delivery device 350 and that can be received by the electronic circuit system 330. For example, in some embodiments, the label 354 can include a passive RFID tag. In other embodiments, the label can include an active RFID tag.

In some embodiments, label 354 can include its own electronic circuit system, similar to the electronic circuit systems described in U.S. patent application Ser. No. 11/621,236, entitled "Devices, Systems and Methods for Medicament Delivery," filed Jan. 9, 2007, which is incorporated herein by reference in its entirety. In such embodiments, the label 354 can produce multiple signals associated with the first medicament delivery device 350 based on the ongoing status of the medicament delivery device 350 as determined by the electronic circuit system included within the label 354. For example, in some embodiments, the first medicament delivery device 350 can include its own electronic circuit system having various switches, sensors or the like, such that when the user completes certain operations (e.g., removing the needle guard, removing the safety tab, etc.), a signal S can be transmitted to the electronic circuit system 330 of the container 310. The electronic circuit system 330 of the container 310 can then output one or more electronic outputs of the type described above to provide information to the user that is unique to the status of the first medicament delivery device 350.

Although the label 354 is shown and described as outputting a signal S that can be received by the electronic circuit system 330, in other embodiments, the label 354 can be a passive device that does not output an electronic signal, but rather, contains information associated with the medicament delivery device 350 in a machine-readable format. For example, in such embodiments, the label 354 can include a bar code portion containing information associated with the medicament delivery device 350. In other embodiments, the label 354 can include a magnetic strip containing information associated with the medicament delivery device 350.

Figure 8:
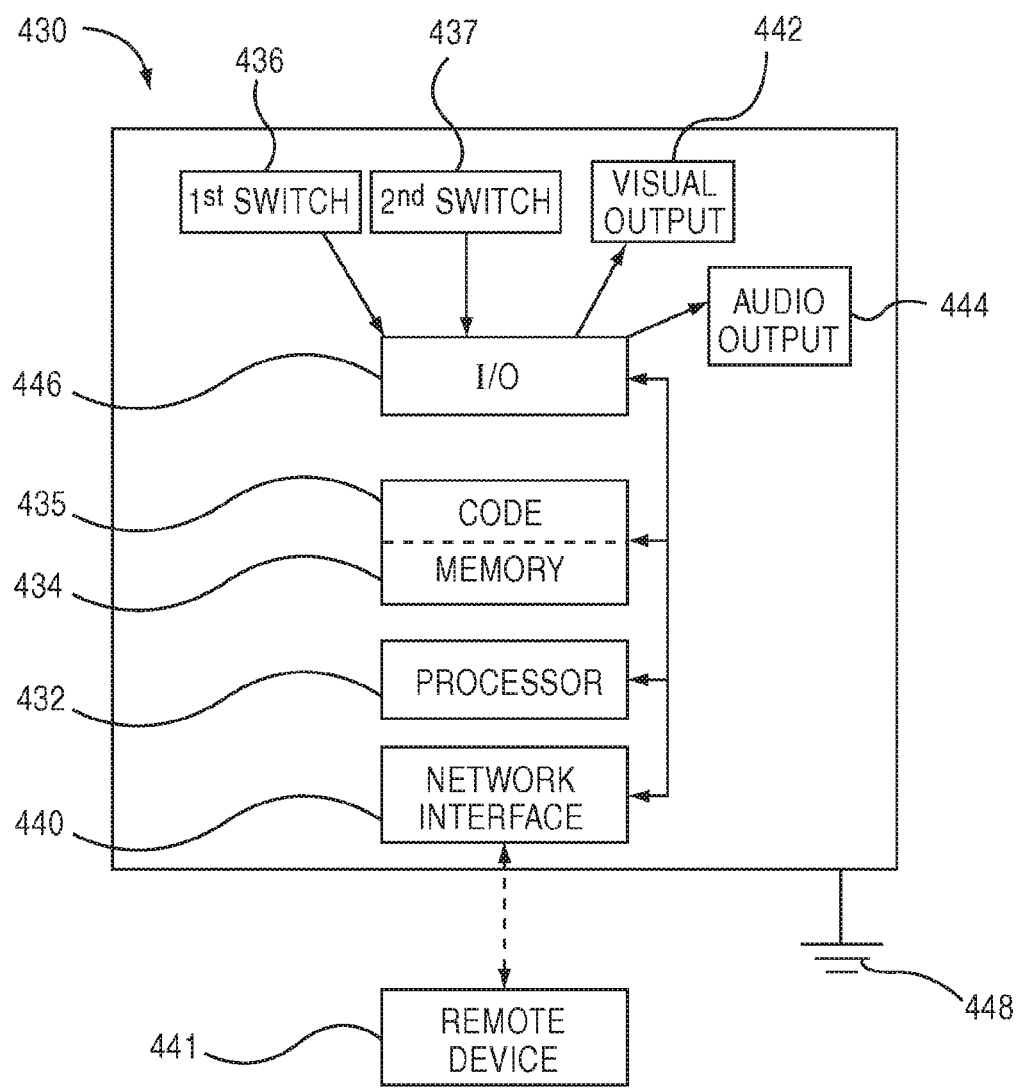
FIG. 8 is a perspective view of a medical device according to an embodiment of the invention in a first configuration.

The electronic circuit systems shown and described above can include many components operatively coupled to perform the functions described herein For example, FIG. 8 is a schematic illustration of an electronic circuit system 430 according to an embodiment of the invention. The electronic circuit system 430 includes a processor 432 operatively coupled to a memory device 434. The memory device 434 can be configured to store processor-readable code 435 instructing the processor 432 to perform the functions described herein. In some embodiments, the processor-readable code 435 can be modified and/or updated as circumstances dictate. The electronic circuit system 430 includes an input/output device 446 configured to receive electronic inputs from a first switch 436 and/or a second switch 437. In some embodiments, the input/output device 446 can receive inputs from an RFID tag (as described above), the user's voice (e.g., through a microphone), a keyboard, a touch screen, a proximity sensor and/or any other suitable device. The input/output device 446 is also configured to provide electronic signals to various output devices, such as, for example, a visual output device 442, an audio output device 444, a haptic output device (not shown in FIG. 8) a wireless receiver (e.g., an RFID tag, a cellular phone system or the like) and/or a wired receiver (e.g., a wired network).

The visual output device 442 can be any suitable device for producing visual indicia, such as, light-emitting diodes (LEDs), liquid-crystal display (LCD) screens, optical polymers, fiber optic components or the like. Similarly, the audio output device 444 can be any suitable device for producing sound, such as a micro-speaker a piezo-electric transducer or the like. Such sound output can include, for example, an alarm, a series of beeps, recorded speech or the like.

In some embodiments, the electronic circuit system 430 includes a network interface 440 configured to operatively couple the electronic circuit system 430 to a remote device 441, either via a wired connection or via a wireless connection. The remote device 441 can be, for example, a remote communications network, a computer, a cell phone, a personal digital assistant (PDA) or the like. Such an arrangement can be used, for example, to download replacement processor-readable code 435 from a central network to the memory device 434. In some embodiments, the electronic circuit system 430 can download information associated with a medicament delivery device, such as an expiration date, a recall notice, updated use instructions or the like.

The network interface 440 can also be configured to transmit information from the electronic circuit system 430 to a central network, such as, for example, an emergency response network. In some embodiments, for example, the electronic circuit system 430 can notify an emergency responder when a medicament delivery device is removed and/or actuated. In other embodiments, the electronic circuit system 430 can transmit information to a third party, such as a physician, an emergency contact and/or the manufacturer of a medicament device, when the medicament delivery device is removed and/or actuated. Such information can include, for example, the location of use, the date and/or time of use or the like.

As shown in FIG. 8, power is supplied to the electronic circuit system 430 by a power source 448. The power source 448 can be any suitable power source, such as, for example, a DC power source and/or an AC power source. In some embodiments, for example, power can be provided to the electronic circuit system 430 by an AC circuit within the building in which the medical device is located. In other embodiments, power can be provided to the electronic circuit system 430 by one or more batteries. In yet other embodiments, power can be provided to the electronic circuit system 430 by both an AC circuit (e.g. as the primary source of power) and by batteries (e.g. as the secondary source of power). In yet other embodiments, the electronic circuit system 430 can be powered by any suitable energy storage device, such as, for example, a capacitor, solar cell or the like.

The processor 432 can be a commercially-available processing device dedicated to performing one or more specific tasks. For example, in some embodiments, the microprocessor 432 can be a commercially-available microprocessor, such as the Sonix SNC 12060 voice synthesizer. Alternatively, the processor 432 can be an application-specific integrated circuit (ASIC) or a combination of ASICs, which are designed to perform one or more specific functions. In yet other embodiments, the processor 132 can be an analog or digital circuit, or a combination of multiple circuits.

The memory device 434 can include one or more types of memory. For example, in some embodiments, the memory device 434 can include a read only memory (ROM) component and a random access memory (RAM) component. The memory device 432 can also include other types of memory suitable for storing data in a form retrievable by the processor 432, for example, electronically-programmable read only memory (EPROM), erasable electronically-programmable read only memory (EEPROM) and/or flash memory.

Although the medical devices shown and described above include one electronic circuit system, in some embodiments, a medical device can include multiple electronic circuit systems configured to perform the functions described herein.

Figure 9:
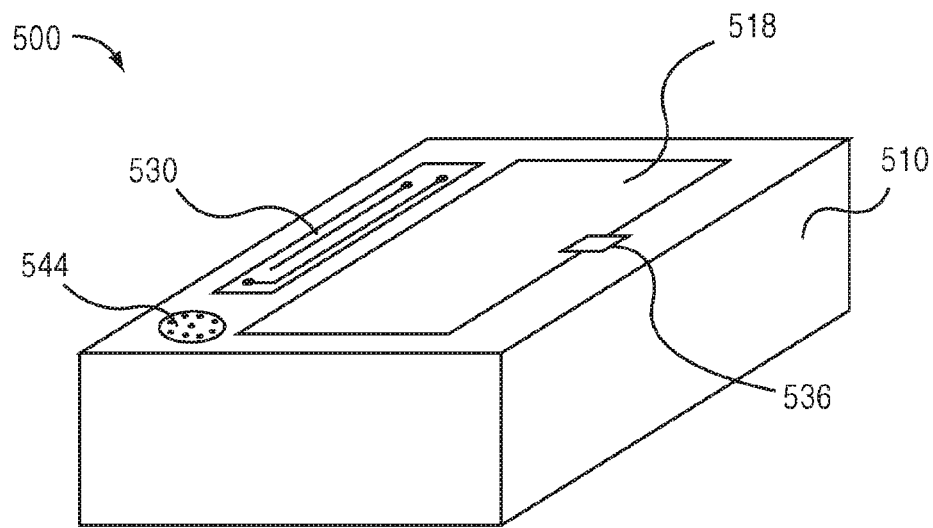
FIG. 9 is a perspective view of the medical device shown in FIG. 8 in a second configuration.
Figure 10:
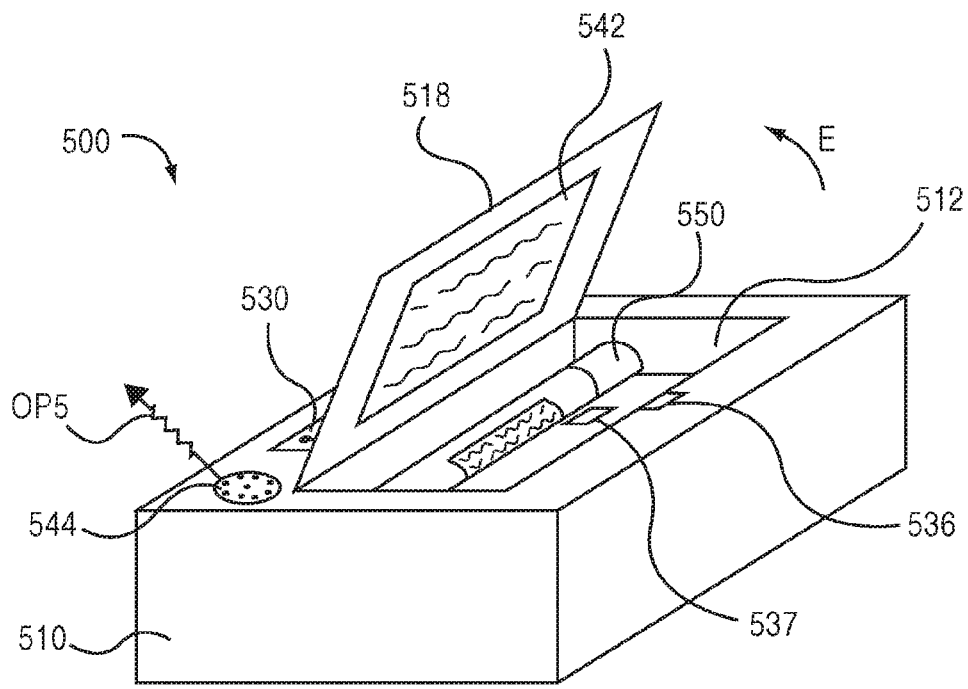
FIG. 10 is a perspective view of the medical device shown in FIG. 8 in a third configuration.
Figure 11:
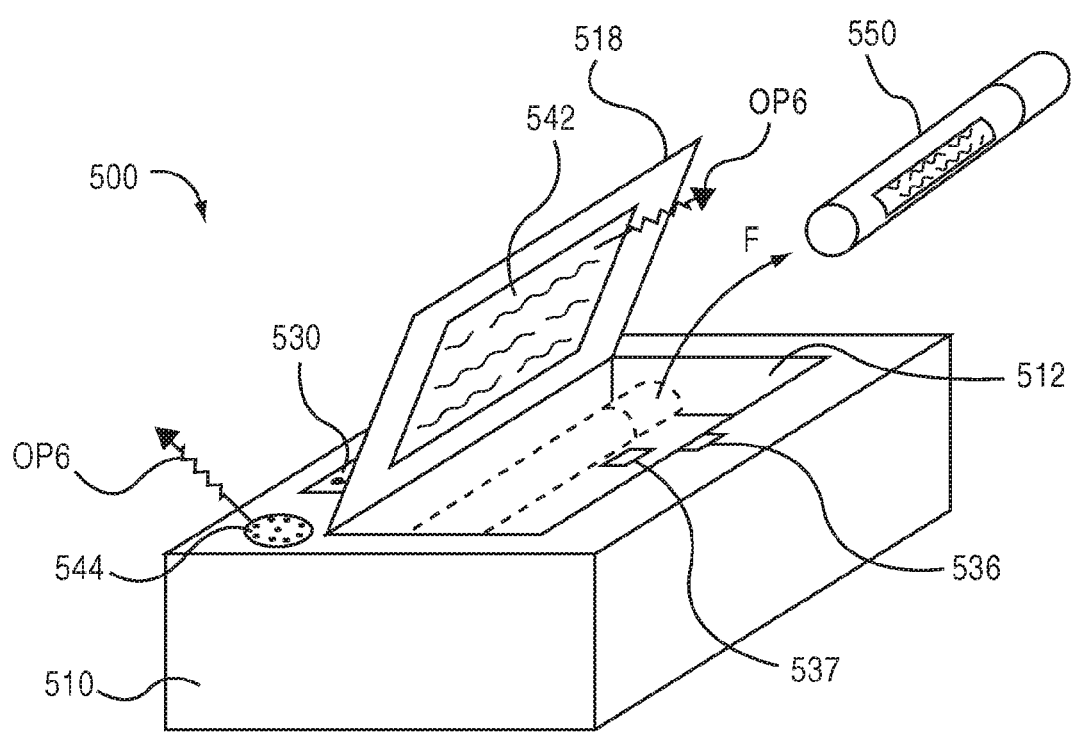
FIG. 11 is a schematic illustration of a portion of a medical device according to an embodiment of the invention.

Although the containers shown and described above include multiple medicament delivery devices, in some embodiments, a container can include only one medicament delivery device. For example, FIGS. 9-11 show a medical device 500 including a container 510 that contains a medicament delivery device 550, such as, for example a pen injector or an auto-injector. As described above, the container 510 defines an internal region 512 in which the medicament delivery device 550 is contained. The container includes an electronic circuit system 530 configured to produce one or more electronic outputs of the type described above. More particularly, the electronic circuit system 530 includes a speaker 544 and an LCD screen 542.

The container 510 also includes a movable portion 518, such as, for example, a hinged lid, that has a first position (see FIG. 9) and a second position (see FIGS. 10-11). When the movable portion 518 is in the first position, the movable portion 518 covers the internal region 512 of the container 510. Conversely, when the movable portion 518 is in the second position, at least a portion of the internal region 512 of the container 510 is exposed. Said another way, when the movable portion 518 is in the second position, the medicament delivery device 550 can be removed from the internal region 512 of the container 510.

The electronic circuit system 530 is operatively coupled to a first switch 536 and a second switch 537. The first switch 536 is configured to move between a first state (e.g., closed) and a second state (e.g., opened) when the movable portion 518 moves between its first position and its second position, as indicated by arrow E in FIG. 10. The electronic circuit system 530 is configured to output a first output OP5 via the speaker 544 when the first switch 536 is moved from its first state to its second state. The first output OP5 can be a recorded speech output associated with an identification of the medicament delivery device 550, an identification of patient symptoms (e.g., instructions for assessing the physical condition of the patient) and/or an instruction for using the medicament delivery device 550. For example, in some embodiments the first output OP5 can state "You have activated the allergic reaction response kit. This kit includes an auto-injector containing DOSE mg of Epinephrine. Before using this auto-injector, please ensure that the patient is exhibiting the following symptoms . . . " Although described as an audible output, in other embodiments, the first output OP5 can be any type of electronic output as described above.

The second switch 537 is configured to move between a first state (e.g., closed) and a second state (e.g., opened) when the medicament delivery device 550 is removed from the internal region 512 of the container 510, as indicated by the arrow F in FIG. 11. The electronic circuit system 530 is configured to output a second output OP6 via the speaker 544 and/or the LCD screen 542 when the second switch 537 is moved from its first state to its second state. The second output OP6 can be, for example, a recorded speech output and/or a video output associated with an identification of the medicament delivery device 550, an identification of patient symptoms (e.g., instructions for assessing the physical condition of the patient) and/or an instruction for using the medicament delivery device 550. For example, in some embodiments the second output OP6 can be an audio-visual output via both the speaker 544 and the LCD screen 542 providing step-by-step instructions for using the medicament delivery device 550.

Although the movable member 518 is shown and described as being a hinged lid, in some embodiments, the movable member can be coupled to the container in any suitable fashion. For example, in some embodiments, the movable member 518 can be a removable cover that is slidingly coupled to the container. In other embodiments, the movable member 518 can be a removable cover that is threadedly coupled to the container (i.e., a removable cap). In yet other embodiments, the movable member 518 can be a removable cover that is coupled to the container via an interference fit. In yet other embodiments, the movable member 518 can be a frangible cover that is irreversibly removed from the container during use of the medical device. For example, in some embodiments the movable member 518 can be a frangible cover that provides a tamperproof seal, a sanitary seal, or the like.

Figure 12:
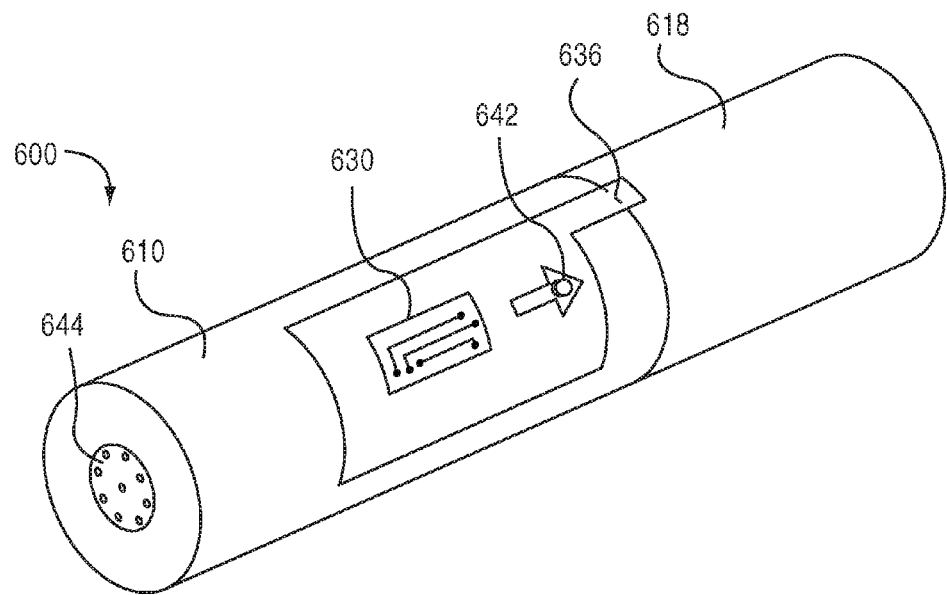
FIGS. 12-14 are schematic illustrations of a medical device according to an embodiment of the invention in a first configuration, a second configuration and a third configuration, respectively.
Figure 13:
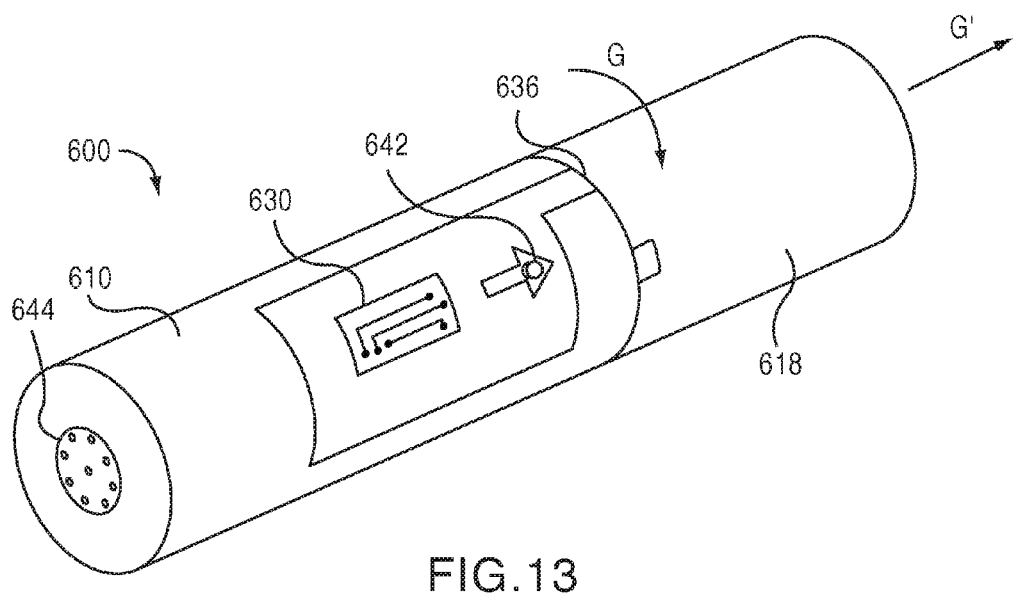
Figure 14:
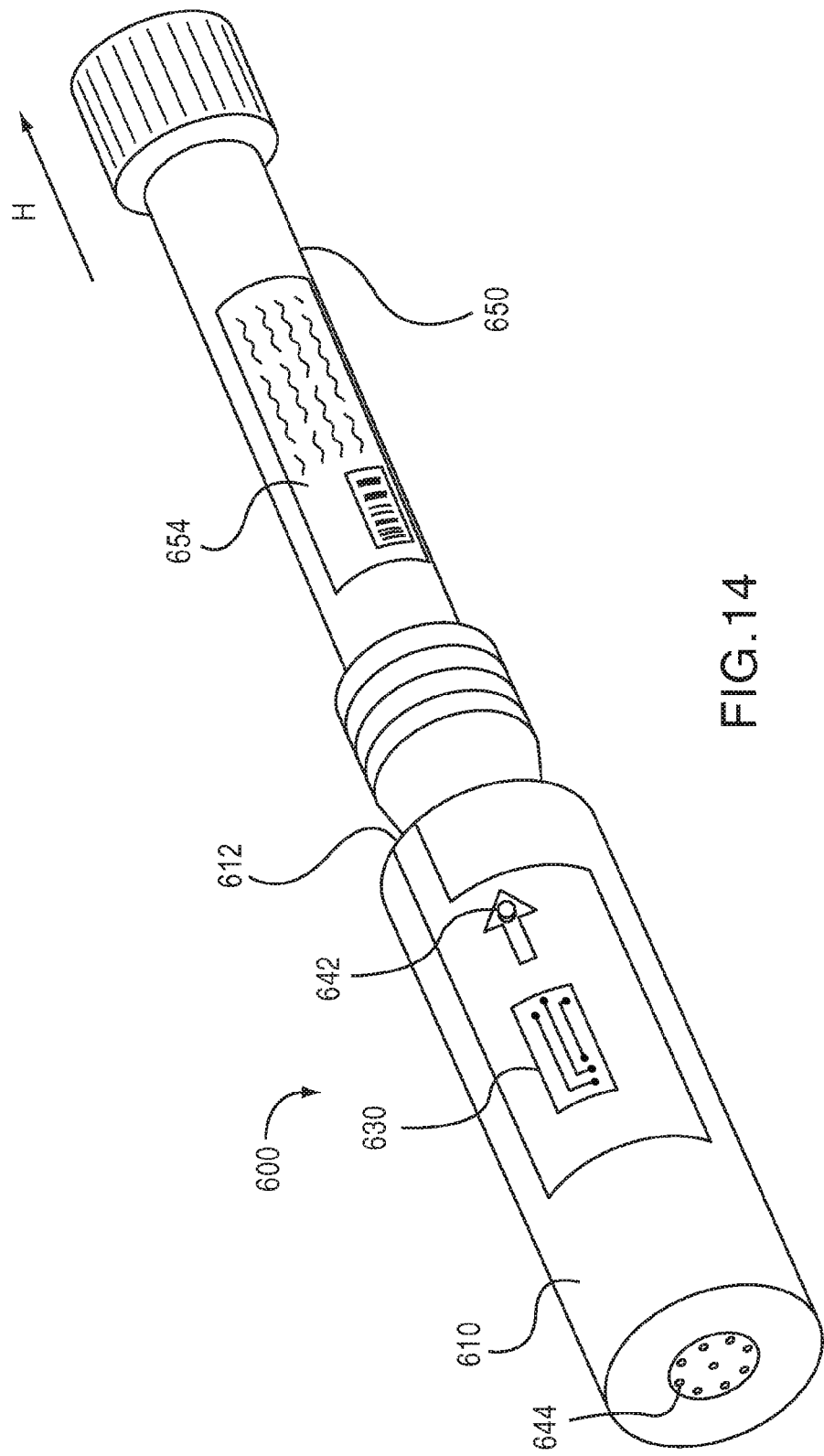

Although the containers are shown and described above as being rigid, box-like containers, in other embodiments, a container can have any suitable shape and/or flexibility. For example, in some embodiments, a container can be a flexible, pouch-like container. Such a container can be more easily carried in certain circumstances, such as, for example at outdoor events (e.g., children's camps, concerts, picnics or the like). In other embodiments, a container can be a tube configured to contain all or a portion of a medicament delivery device. For example, FIGS. 12-14 show a medical device 600 including a tube-shaped container 610 and a retainer 618. The container 610 defines an internal region 612 (see FIG. 15) in which at least a portion of a medicament delivery device 650 can be contained.

The retainer 618, which can be, for example, a mating tube-shaped lid, is movably coupled to the container 610 to retain the medicament delivery device 650 within the internal region 612. Said another way, the retainer 618 has a first position (FIG. 12) and a second position (FIG. 13). When the retainer 618 is in the first position, the retainer 618 prevents the medicament delivery device 650 from being removed from the internal region 612 of the container 610. When the retainer 618 is in the second position, the medicament delivery device 650 can be removed from the internal region 612 of the container 610.

The medical device 600 includes an electronic circuit system 630 coupled to the container 610. The electronic circuit system 630 includes a speaker 644 and a light emitting diode (LED) 642 for providing an electronic output associated with the use of the medicament delivery device 650, as described herein. In some embodiments, the electronic circuit system can be, for example, a flexible circuit included in a label coupled to an outer surface of the container 610, similar to the electronic circuit systems described in U.S. patent application Ser. No. 11/621,236, entitled "Devices, Systems and Methods for Medicament Delivery," filed Jan. 9, 2007, which is incorporated herein by reference in its entirety.

The electronic circuit system 630 is configured to output a first electronic output via the LED 642 and/or the speaker 644 when the retainer 618 is moved relative to the container 610, as indicated by arrows G and/or G' in FIG. 13. As described above, the first electronic output can be associated with an identification of the medicament delivery device 650, an identification of a physical condition and/or an instruction for using the medicament delivery device 650. For example, in some embodiments, the first electronic output can be associated with an audible message instructing a user in the use of the medicament delivery device 650. Such an audible message can state, for example, "You have activated an interactive auto-injector containing DOSE mg of Epinephrine. Please remove the top of the container by twisting and pulling as indicated by the flashing arrow. After removing the top of the container, please remove the auto-injector from the container by firmly pulling on the exposed end of the auto-injector."

The electronic circuit system 630 can be prompted to output the first electronic output by a switch 636 configured to change states when the retainer 618 is moved relative to the container 610. The switch 636 can be any suitable electronic switch having at least two states. For example, in some embodiments, the switch 636 can be a single-use "tear-through" switch, as described in U.S. patent application Ser. No. 11/621,236, entitled "Devices, Systems and Methods for Medicament Delivery," filed Jan. 9, 2007, which is incorporated herein by reference in its entirety. For example, the switch 636 can be irreversibly moved from a first state to a second state when the retainer 618 is moved relative to the container 610. In other embodiments, a switch can be a multi-use switch, such as a microswitch.

Similarly, the electronic circuit system 630 is configured to output a second electronic output via the LED 642 and/or the speaker 644 when the medicament delivery device 650 is removed from the internal region 612 defined by the container 610, as shown by arrow H in FIG. 14. The second electronic output can be associated with an identification of the medicament delivery device 650, an identification of a physical condition and/or an instruction for using the medicament delivery device 650. For example, in some embodiments, the second electronic output can be an audible message stating, "To activate the auto-injector, first remove the needle guard. The needle guard is at the bottom of the auto-injector and contains the number one inside of an arrow pointing downward. Remove the needle guard by pulling in the direction of the arrow."

As shown in FIG. 14, the medicament delivery device 650 includes a label 654 containing information associated with the medicament delivery device 650 arranged in a machine-readable format. The electronic circuit system 630 is configured to receive (e.g., "read") the information contained in the label 654 and include at least a portion of the information in the first electronic output and/or the second electronic output. In this manner, the electronic circuit system 630 can be configured to produce an electronic output that is unique to the medicament delivery device 650 contained within the container 610. This arrangement allows the container 610 to be reused with any number of different medicament delivery devices 650. Moreover, this arrangement allows the container 610 to track the usage of a chronic-care medicament delivery devices. For example, in some embodiments, the electronic circuit system 630 can track each use of the medicament delivery device 650 and log such information on the label 654.

The label 654 can be any device suitable for containing information associated with the medicament delivery device 650 in a machine-readable format. For example, in some embodiments, the label 654 can include a bar code portion containing information associated with the medicament delivery device 650. In other embodiments, the label 654 can include a magnetic strip containing information associated with the medicament delivery device 650. In yet other embodiments, the label 654 can include a passive RFID tag containing information associated with the medicament delivery device 650. In yet other embodiments, the label 654 can include an active RFID tag containing information associated with the medicament delivery device 650.

Although the retainer 618 is shown as covering the internal region 612 defined by the container 610, in some embodiments, the retainer 618 can allow access to the internal region 612 while still retaining the medicament delivery device 650 within the internal region 612. For example, in some embodiments, the retainer 618 can be a clip, a strap or the like.

Although the medicament delivery device 650 is shown in FIGS. 12-13 as being disposed entirely within the container 610 and the retainer 618, in some embodiments, only a portion of the medicament delivery device 650 is disposed within the container 610 and/or the retainer 618. For example, in some embodiments, a container can be a sleeve configured to be disposed about a portion of a medicament delivery device, such as a chronic care pen injector. The retainer can function to retain the pen injector within the sleeve and/or to prevent the pen injector from being actuated (e.g., the retainer can act as a locking member). In use, the user can activate the electronic circuit system by depressing a start button disposed on the container. Alternatively, in some embodiments, the electronic circuit system can be activated by removing the retainer from the pen injector and/or the container. In yet other embodiments, the electronic circuit system can be activated by moving the pen injector relative to the container (i.e., twisting the pen injector within the container). Upon activation, the electronic circuit system then "reads" a label and outputs a first electronic output and/or a second electronic output, as described above.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although electronic circuit systems are shown and described above as outputting one or more outputs directed towards a single, immediate user, in some embodiments, an electronic circuit system can output multiple outputs directed towards multiple different classes of users. For example, in some embodiments, an electronic circuit system can output a first electronic output to the immediate user and second electronic output to a remotely located emergency response team. In such embodiments, the second electronic output can be, for example, a phone call, a page, an e-mail or the like. For example, in some embodiments, the second electronic output can be an e-mail to the parents and/or caregivers of a child. Moreover, such a second electronic output can be transmitted either wirelessly or through a wired network.

Although the electronic circuit systems are shown and described above as outputting one or more outputs in response to one or more switches, in other embodiments an electronic circuit system can output an electronic output in response to any number of different inputs. For example, in some embodiments, an electronic circuit system can output an electronic output based on input from the user provided via a keyboard, a touch screen, a microphone or any other suitable input device. In this manner, the electronic outputs can be produced in response to direct feedback from the user.

In other embodiments, an electronic circuit system can output an electronic output based on a sensor included in the container and/or the medicament delivery device. Such a sensor can include, for example, a proximity sensor (e.g., to determine the position of the medicament delivery device), a temperature sensor, a pressure sensor, an optical sensor or the like. For example, in some embodiments, the container can include a temperature sensor configured to sense the temperature of the medicament contained within the medicament delivery device. In this manner, the electronic circuit system can output an instruction and/or a status message when the medicament is too cold for effective delivery. For example, in some embodiments, when the medicament is too cold for effective delivery (this may occur, for example, if the container is being used in an outdoor setting), the electronic circuit system can output a message, such as, for example, "Medicament is too cold—please briskly rub the auto-injector between your hands before using."

Although the electronic circuit systems are shown and described above as outputting a single electronic output in response to an input (e.g., the removal of a medicament delivery device, the change in position of a hinged lid, etc.), in some embodiments, an electronic circuit system can output a sequence of electronic outputs in response to such an input. In some embodiments, for example, when a medicament delivery device is removed from a container, an electronic circuit system can output a predetermined sequence of use instructions over a predetermined time period. For example, upon removing the medicament delivery device, the first instruction can be an audible output indicating the type of medicament delivery device removed. After a predetermined time period, the electronic circuit system can then output a second instruction, which can be a visual output instructing the user in how to diagnose the patient and/or prepare the patient for the medicament. In a similar manner, the electronic circuit system can provide additional outputs to instruct the user in the use of the medicament delivery device. Moreover, in some embodiments, the electronic circuit system can output an electronic output instructing the user in post-use procedures, such as for example, the disposal of the medicament delivery device, instructions for follow-up treatment or the like.

For example, although the electronic circuit systems are shown and described above as being configured to output primarily audible and visual outputs, in other embodiments, an electronic circuit system can be configured to produce any suitable output. For example, in some embodiments, an electronic circuit system can produce a haptic output, such as a vibratory output produced by a piezo-electric actuator. In other embodiments, an electronic circuit system can produce a thermal output, produced by a heating or cooling element.

Although the electronic circuit systems are shown and described above as outputting recorded speech in English, in other embodiments, the electronic circuit system can output recorded speech in any language. In yet other embodiments, the electronic circuit system can output recorded speech in multiple languages. In yet other embodiments, the user can select the language in which the recorded speech is to be output.

Although the medicament delivery devices have been shown and described above as being primarily single-use medical injectors, in some embodiments a medicament delivery device can include any suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system can output instructions associated with not only an initial use of the medicament delivery device, but also associated with repeated uses, dosage monitoring or the like. In other embodiments, a medicament delivery device can include a transdermal medicament delivery device, an inhaler or a nasal medicament delivery device.

Although various embodiments have been described as having particular features and/or combinations of components, other embodiments are possible having a combination of any features and/or components from any of embodiments where appropriate. For example, in some embodiments a medical device can include a container including an electronic circuit system, two or more medicament delivery devices and a movable portion. In such embodiments, each of the medicament delivery devices can be associated with a switch. Moreover, the movable portion can also be associated with a switch. In this manner, the electronic circuit system can be configured to output a first electronic output when the movable portion is moved, a second electronic output when the first medicament delivery device is removed from the container and a third electronic output when the second medicament delivery device is removed from the container.

What is claimed is:

1. An apparatus, comprising:
a container defining an internal region configured to contain at least a portion of a medicament delivery device, the container including an electronic circuit system including a switch, the electronic circuit system configured to receive an input from at least one of a microphone or an electronic visual display, the electronic circuit system configured to output a first electronic output associated with the input, the electronic circuit system configured to output a second electronic output associated with the medicament delivery device when the switch is moved from a first state to a second state, the container including a mounting portion configured to be coupled to a structure such that the electronic circuit system is operably coupled to a power source associated with the structure; and
a movable member configured to be movably coupled to the container, the movable member configured to maintain the portion of the medicament delivery device within the internal region, a portion of the movable member configured to move the switch from the first state to the second state when the movable member is moved relative to the container.

2. The apparatus of claim 1, wherein at least one of the first electronic output or the second electronic output is associated with at least one of an identification of the medicament delivery device, an identification of a physical condition or an instruction for using the medicament delivery device.

3. The apparatus of claim 1, wherein at least one of the first electronic output or the second electronic output is a wireless communications signal.

4. The apparatus of claim 1, further comprising;
the electronic visual display, at least one of the first electronic output or the second electronic output includes a visual output produced by the electronic visual display.

5. The apparatus of claim 1, wherein at least one of the first electronic output or the second electronic output includes a recorded speech output.

6. The apparatus of claim 1, wherein the switch is a first switch, the electronic circuit system includes a second switch, the apparatus further comprising:
a retainer configured to retain the medicament delivery device within the internal region, the electronic circuit system includes a second switch associated with the retainer, a portion of the retainer configured to move the second switch between a first state and a second state when the retainer is moved relative to the container, the electronic circuit system configured to output a third electronic output when the second switch moves between its first state and its second state.

7. The apparatus of claim 1, wherein:
the medicament delivery device includes a label configured to output a signal configured to be received by the electronic circuit system, the signal associated with at least one of a location of the medicament delivery device, a contents of the medicament delivery device, an expiration date of the medicament delivery device, a dosage of the medicament delivery device or a use instruction associated with the medicament delivery device; and
at least one of the first electronic output or the second electronic output is associated with the signal received by the electronic circuit system.

8. The apparatus of claim 1, further comprising:
the electronic visual display coupled to the movable member, at least one of the first electronic output or the second electronic output includes a visual output produced by the electronic visual display.

9. An apparatus, comprising:
a container defining an internal region configured to contain at least a portion of a medicament delivery device, the container including a mounting portion;
a movable member configured to be movably coupled to the container, the movable member configured to limit movement of the medicament delivery device; and
an electronic circuit system coupled to the container, the mounting portion of the container configured to be coupled to a structure such that the electronic circuit system is operably coupled to a power source associated with the structure, the electronic circuit system including an electronic visual display and a speaker, the electronic circuit system configured to produce a first output via at least one of the electronic visual display or the speaker, the electronic circuit system configured to produce a second output in response to an input received from at least one of a microphone or the electronic visual display, the electronic circuit system configured to produce a third output when the movable member is moved.

10. The apparatus of claim 9, wherein the electronic visual display is coupled to the movable member.

11. The apparatus of claim 9, wherein at least one of the second output or the third output includes a wireless communications signal.

12. The apparatus of claim 9, wherein at least one of the first output, the second output or the third output includes a recorded speech output.

13. The apparatus of claim 9, wherein:
the electronic circuit system including a switch disposed on a printed circuit board, the electronic circuit system configured to produce the third output when the switch is moved from a first state to a second state; and
the movable member is configured to retain a portion of the medicament delivery device within the internal region, a portion of the movable member configured to engage a portion of the printed circuit board to move the switch from the first state to the second state when the movable member is moved relative to the container.

14. The apparatus of claim 9, further comprising:
a battery disposed within the container, the battery configured to be operably coupled to the electronic circuit system.

15. An apparatus, comprising:
a container defining an internal region configured to contain at least a portion of a medicament delivery device, the container including a mounting portion;
a movable member configured to be movably coupled to the container, the movable member configured to limit movement of the medicament delivery device; and
an electronic circuit system coupled to the container, the mounting portion of the container configured to be coupled to a structure such that the electronic circuit system is operably coupled to a power source associated with the structure, the electronic circuit system including a switch and an electronic visual display, the electronic circuit system configured to receive an input from at least one of a microphone or the electronic visual display, the electronic circuit system configured to produce a first electronic output associated with the input, the electronic circuit system configured to produce a second electronic output when the switch is moved from a first state to a second state,
a portion of the movable member configured to move the switch from the first state to the second state when the movable member is moved relative to the container.

16. The apparatus of claim 15, wherein the electronic visual display is coupled to the movable member.

17. The apparatus of claim 15, further comprising:
a battery disposed within the container, the battery configured to be operably coupled to the electronic circuit system.

* * * * *